(12) United States Patent
Han

(10) Patent No.: US 11,299,713 B2
(45) Date of Patent: Apr. 12, 2022

(54) CELL LINE FOR PRODUCING ADENOVIRUS AND METHOD OF PREPARING THE SAME

(71) Applicant: GENEUIN-TECH CO., LTD., Gimhae (KR)

(72) Inventor: Eun Yeong Han, Gimhae (KR)

(73) Assignee: GENEUIN-TECH CO., LTD., Gimhae (KR)

( * ) Notice: Subject to any disclaimer, the term of this patent is extended or adjusted under 35 U.S.C. 154(b) by 0 days.

(21) Appl. No.: 16/653,171

(22) Filed: Oct. 15, 2019

(65) Prior Publication Data

US 2020/0172873 A1 Jun. 4, 2020

Related U.S. Application Data

(63) Continuation of application No. PCT/KR2018/004701, filed on Apr. 23, 2018.

(30) Foreign Application Priority Data

Apr. 21, 2017 (KR) .................. 10-2017-0051829

(51) Int. Cl.
| | |
|---|---|
| C12N 7/00 | (2006.01) |
| C12N 15/86 | (2006.01) |
| C12N 5/10 | (2006.01) |
| C12N 5/16 | (2006.01) |
| C12N 5/071 | (2010.01) |
| A61K 35/761 | (2015.01) |
| C07K 14/005 | (2006.01) |
| A61K 48/00 | (2006.01) |

(52) U.S. Cl.
CPC .......... *C12N 5/0688* (2013.01); *A61K 35/761* (2013.01); *C07K 14/005* (2013.01); *C12N 7/00* (2013.01); *C12N 15/86* (2013.01); *A61K 48/00* (2013.01); *C12N 2710/10021* (2013.01); *C12N 2710/10022* (2013.01); *C12N 2710/10034* (2013.01); *C12N 2710/10043* (2013.01); *C12N 2710/10052* (2013.01); *C12N 2740/10043* (2013.01)

(58) Field of Classification Search
None
See application file for complete search history.

(56) References Cited

U.S. PATENT DOCUMENTS

| | | | |
|---|---|---|---|
| 5,853,631 A | 12/1998 | Linehan | |
| 6,558,948 B1 | 5/2003 | Kochanek et al. | |
| 7,074,618 B2 | 7/2006 | Li et al. | |
| 7,816,104 B2 | 10/2010 | Vogels et al. | |
| 7,851,218 B2 | 12/2010 | Howe et al. | |
| 2002/0090717 A1 | 7/2002 | Gao et al. | |
| 2004/0191222 A1 | 9/2004 | Emini et al. | |
| 2004/0235174 A1 | 11/2004 | Grimm et al. | |
| 2005/0003506 A1 | 1/2005 | Li et al. | |
| 2005/0045097 A1 | 3/2005 | Suitor et al. | |
| 2006/0270041 A1 | 11/2006 | Howe et al. | |
| 2008/0056198 A1 | 3/2008 | Charpentier et al. | |
| 2014/0308704 A1 | 10/2014 | Yu et al. | |

FOREIGN PATENT DOCUMENTS

| | | |
|---|---|---|
| CA | 2283253 A1 | 9/1998 |
| JP | 2003-510089 A | 3/2003 |
| JP | 2008-522630 A | 7/2008 |
| KR | 10-047018 B1 | 2/2005 |
| KR | 10-2006-0095557 A | 8/2006 |
| KR | 10-2013-0057950 A | 6/2013 |
| KR | 10-2014-0118511 A | 10/2014 |
| WO | 97/00326 A1 | 1/1997 |
| WO | 01/05945 A2 | 1/2001 |

OTHER PUBLICATIONS

Seo et al. Development of replication-competent adenovirus for bladder cancer by controlling adenovirus E1a and E4 gene expression with the survivin promoter. Oncotarget, 2014, 5(14): 5615-5623.*
International Search Report, PCT Application No. PCT/KR2018/004701, dated Jul. 25, 2018, 6 pages.
Matsushita T., et al., "The adenovirus E1A and E1B19K genes provide a helper function for transfection-based adeno-associated virus vector production," Journal of General Virology, vol. 85: 2209-2214 (2004).
Office Action, KR Application No. 2018-0046947, dated Feb. 28, 2020, 11 pages.
Office Action, KR Application No. 2018-0046947, dated Mar. 28, 2019, 8 pages.
Office Action, KR Application No. 2018-0046947, dated May 29, 2020, 3 pages.
Office Action, KR Application No. 2019-0054108, dated Aug. 6, 2019, 11 pages.
Office Action, KR Application No. 2019-0054108, dated Feb. 28, 2020, 7 pages.
Kovesdi et al., "Adenoviral Producer Cells," Viruses, 2010, 2, 1681-1703.
Search Report, EP Application 18787809.5, dated Dec. 7, 2020, 9 pages.

\* cited by examiner

*Primary Examiner* — Nianxiang Zou
(74) *Attorney, Agent, or Firm* — United One Law Group LLC; Kongsik Kim; Jhongwoo Peck

(57) ABSTRACT

The present invention relates to a cell line for producing an adenovirus having a limited autoreplication capability, and a method of preparing the same, and more particularly, to a cell line for producing an adenovirus having no autoreplication capability by expressing at least one selected from an adenoviral E1 protein and an E1A or E1B protein, and a method of preparing the same. Also, the present invention relates to the use of the cell line expressing at least one selected from the adenoviral E1 protein and the E1A or E1B protein.

13 Claims, 12 Drawing Sheets
Specification includes a Sequence Listing.

FIG. 2

E1A (998bp)  SEQ ID NO: 1 ggatccatgagacatattatctgccacggaggtgttattaccgaagaaatg
gccgccagtcttttggaccagctgatcgaagaggtactggctgataatctt
ccacctcctagccattttgaaccacctacccttcacgaactgtatgatttaga
cgtgacggcccccgaagatcccaacgaggaggcggtttcgcagattttc
ccgactctgtaatgttggcggtgcaggaagggattgacttactcactttcc
gccggcgcccggttctccggagccgcctcacctttcccggcagcccgag
cagccggagcagagagccttgggtccggtttctatgccaaaccttgtacc
ggaggtgatcgatcttacctgccacgaggctggctttccacccagtgacga
cgaggatgaagagggtgaggagtttgtgttagattatgtggagcacccgg
gcacggttgcaggtcttgtcattatcaccggaggaatacggggacccag
atattatgtgttcgctttgctatatgaggacctgtggcatgtttgtctacagtaa
gtgaaaattatgggcagtgggtgatagagtggtgggtttggtgtggtaattt
ttttttaattttacagttttgtggtttaaagaattttgtattgtgatttttttaaaag
gtcctgtgtctgaacctgagcctgagcccgagccagaaccggagcctgca
agacctacccgccgtcctaaaatggcgcctgctatcctgagacgcccgac
atcacctgtgtctagagaatgcaatagtagtacggatagctgtgactccgg
tccttctaacacacctcctgagatacacccggtggtcccgctgtgcccatta
aaccagttgccgtgagagttggtgggcgtcgccaggctgtggaatgtatc
gaggacttgcttaacgagcctgggcaacctttggacttgagctgtaaacgc
cccaggccataagaattc

FIG. 3

E1B (1808bp)                                    SEQ ID NO: 2 ggatccatggaggcttgggagtgtttggaagattttctgctgtgcgtaac
ttgctggaacagagctctaacagtacctcttggttttggaggtttctgtgggg
ctcatcccaggcaaagttagtctgcagaattaaggaggattacaagtggga
atttgaagagcttttgaaatcctgtggtgagctgtttgattctttgaatctgg
gtcaccaggcgcttttccaagagaaggtcatcaagactttggattttccac
accggggcgcgctgcggctgctgttgcttttttgagttttataaaggataaa
tggagcgaagaaacccatctgagcggggggtacctgctggattttctggc
catgcatctgtggagagcggttgtgagacacaagaatcgcctgctactgtt
gtcttccgtccgcccggcgataataccgacggaggagcagcagcagcag
caggaggaagccaggcggcggcggcaggagcagagcccatggaacc
cgagagccggcctggaccctcgggaatgaatgttgtacaggtggctgaa
ctgtatccagaactgagacgcattttgacaattacagaggatgggcaggg
gctaaaggggtaaagagggagcggggggcttgtgaggctacagagga
ggctaggaatctagcttttagcttaatgaccagacaccgtcctgagtgtat
tacttttcaacagatcaaggataattgcgctaatgagcttgatctgctggcg
cagaagtattccatagagcagctgaccacttactggctgcagccagggga
tgattttgaggaggctattagggtatatgcaaaggtggcacttaggccagat
tgcaagtacaagatcagcaaacttgtaaatatcaggaattgttgctacatt
tctgggaacggggccgaggtggagatagatacggaggatagggtggc
ctttagatgtagcatgataaatatgtggccgggggtgcttggcatggacgg
ggtggttattatgaatgtaaggtttactggccccaattttagcggtacggtttt
cctggccaataccaaccttatcctacacggtgtaagcttctatgggtttaac
aatacctgtgtggaagcctggaccgatgtaagggttcggggctgtgcctt
ttactgctgctggaaggggtggtgtgtcgcccaaaagcagggcttcaat
taagaaatgcctcttgaaaggtgtaccttgggtatcctgtctgagggtaact
ccagggtgcgccacaatgtggcctccgactgtggttgcttcatgctagtg
aaaagcgtggctgtgattaagcataacatggtatgtggcaactgcgagga
cagggcctctcagatgctgacctgctcggacggcaactgtcacctgctga
agaccattcacgtagccagccactctcgcaaggcctggccagtgtttgag
cataacatactgacccgctgttccttgcatttgggtaacaggagggggtgt
tcctaccttaccaatgcaatttgagtcacactaagatattgcttgagcccgag
agcatgtccaaggtgaacctgaacggggtgtttgacatgaccatgaaga
tctggaaggtgctgaggtacgatgagacccgcaccaggtgcagaccctg
cgagtgtggcggtaaacatattaggaaccagcctgtgatgctggatgtga
ccgaggagctgaggcccgatcacttggtgctggcctgcacccgcgctga
gtttggctctagcgatgaagatacagattgagaattc (a)

(b)

(a)

| Cell line (L132) | Ct Value | Log Value | Value |
|---|---|---|---|
| #5 | 29.425 | 5.28 | 188835.0 |
| #6 | 28.625 | 5.51 | 320451.6 |
| #10 | 29.285 | 5.32 | 207146.0 |
| #11 | 28.05 | 5.67 | 468646.1 |

(b)

E1 (241bp)

CELL LINE FOR PRODUCING ADENOVIRUS AND METHOD OF PREPARING THE SAME

CROSS-REFERENCE TO RELATED APPLICATIONS

This application is a continuation application of International Application No. PCT/KR2018/004701 filed on Apr. 23, 2018, which claims priority to Korean Application No. 10-2017-0051829 filed on Apr. 21, 2017. The applications are incorporated herein by reference.

TECHNICAL FIELD

The present invention relates to a novel cell line for producing an adenovirus having a reduced autoreplication capability; a method of preparing the same; and the use of the cell line.

BACKGROUND ART

Vectors are most commonly used as delivery systems in which a gene is delivered to cells and delivered in vivo to apply the gene to clinical trials for gene therapy.

The vectors generally include non-viral vectors in which nucleic acids such as DNA and RNA are used by themselves, and viral vectors including Adeno, Retro, pox, vaccinia, herpes, and the like. Among these, Adeno is most commonly used in clinical trials for gene therapy.

Adenoviruses carrying double-stranded DNA have a high expression level in both dividing and non-dividing cells. Also, the adenoviruses have an advantage in that they have few limitations in insertion of foreign genes.

However, the presence of replication-competent adenovirus (RCA) is one of the most serious problems caused when an adenovirus is used as a gene delivery vector. The RCA may be produced by recombination or contamination with host DNA sequences in various steps of a preparation process. When there is even a small number of an RCA, the RCA can replicate autonomously in human tissues and circulate to other sites, thereby causing serious side effects in immunodeficient patients.

Therefore, there is a need for production of a cell line producing a recombinant adenovirus having a reduced autoreplication capability, in which no RCA is produced, thereby solving the above problems.

SUMMARY

One aspect of the present invention is to provide a cell line for producing a recombinant adenovirus having a reduced autoreplication capability, in which no RCA is produced.

Another aspect of the present invention is to provide a method of preparing a cell line for producing the adenovirus having a reduced autoreplication capability, and the use of the cell line.

To achieve the above object, according to one aspect of the present invention, there are provided a cell line for producing an adenovirus having a reduced autoreplication capability; a method of preparing the cell line for producing an adenovirus having a reduced autoreplication capability; and various uses of the cell line for producing an adenovirus having a reduced autoreplication capability.

One exemplary embodiment of the present invention provides a cell line for producing an adenovirus. The cell line includes:

an E1 gene or an expression product thereof; and
an E1A gene or an expression product thereof, an E1B gene or an expression product thereof, or both.

According to one exemplary embodiment of the present invention, the E1 protein may be an E1 protein of adenovirus type 5.

According to another exemplary embodiment of the present invention, the nucleic acid sequence encoding the E1A protein may be represented by SEQ ID NO: 1.

According to still another exemplary embodiment of the present invention, the nucleic acid sequence encoding the E1B protein may be represented by SEQ ID NO: 2.

According to one exemplary embodiment of the present invention, the cell line may be a human-derived cell line.

According to one exemplary embodiment of the present invention, the cell line may be an L132 cell line.

The cell line for producing an adenovirus according to the present invention is characterized in that the cell line may be safely used for therapeutic applications because the autoreplication capability of the adenovirus itself is lost, and an RCA is not produced.

Also, the present invention provides a packaging system for producing a recombinant adenovirus, which includes the cell line for producing an adenovirus; and an adenoviral vector.

In addition, in order to prepare a cell line for producing an adenovirus, the present invention provides a method of preparing a cell line for producing an adenovirus, which includes:

(a) preparing retrovirus vectors comprising nucleic acid sequences of adenoviral E1, E1A and E1B genes, respectively;

(b) transfecting the respective retrovirus vectors into cell lines for producing retroviruses to produce respective retroviruses;

(c) infecting a cell line for producing an adenovirus with the retrovirus produced in (b), which includes the nucleic acid sequence of the E1 gene; and (d) further infecting the cell line for producing an adenovirus of (c) with the retroviruse produced in (b), which includes the nucleic acid sequence of the E1A gene, the retrovirus produced in (b), which includes the nucleic acid sequence of the E1B gene, or both, to obtain the cell line for producing the adenovirus having a reduced autoreplication capability.

According to an exemplary embodiment of the present invention, the E1A gene may be represented by SEQ ID NO: 1.

According to another exemplary embodiment of the present invention, the E1B gene may be represented by SEQ ID NO: 2.

According to still another exemplary embodiment of the present invention, the cell line for producing an adenovirus may be a human-derived cell line. As one preferred example, the cell line may be an L132 cell line.

Also, the present invention provides various uses of the adenovirus obtained from the cell line produced by the method.

According to one exemplary embodiment of the present invention, there is provided a packaging system for producing an adeno-associated virus (AAV), which includes:

an adenovirus obtained from the cell line produced by the method described above;

a cell line including a nucleic acid sequence of a rep gene of the AAV and a nucleic acid sequence of a cap gene of the AAV; and an AAV vector.

According to another exemplary embodiment of the present invention, there is provided a gene therapeutic agent including the adenovirus obtained from the cell line produced by the method described above.

Further, the present invention provides various uses of the cell line described above.

According to one exemplary embodiment of the present invention, there is provided a cell line for producing an antibody, which further includes:

a nucleic acid sequence of an E1 gene; and a nucleic acid sequence of at least one selected from nucleic acid sequences of E1A and E1B genes.

According to one exemplary embodiment of the present invention, there is provided a cell line for producing a vaccine, which further includes:

a nucleic acid sequence of an E1 gene; and a nucleic acid sequence of at least one selected from nucleic acid sequences of E1A and E1B genes.

That is, the cell line of the present invention may be used to produce antibodies or vaccines.

The present invention relates to a cell line for producing an adenovirus having a reduced autoreplication capability. Therefore, the cell line of the present invention can be used to provide a cell line for producing a recombinant adenovirus having a reduced autoreplication capability, in which an RCA is not produced, and can also be used to provide a cell line having a superior ability to produce an adenovirus (hereinafter referred to as a 'adenovirus-producing ability') having a reduced autoreplication capability, compared to the existing cell lines for producing an adenovirus having a reduced autoreplication capability, in which an RCA is not produced.

BRIEF DESCRIPTION OF DRAWINGS

FIG. 2 shows a sequence of an adenoviral E1A gene used in the present invention.

FIG. 3 shows a sequence of an adenoviral E1B gene used in the present invention.

DETAILED DESCRIPTION

Figure 1:
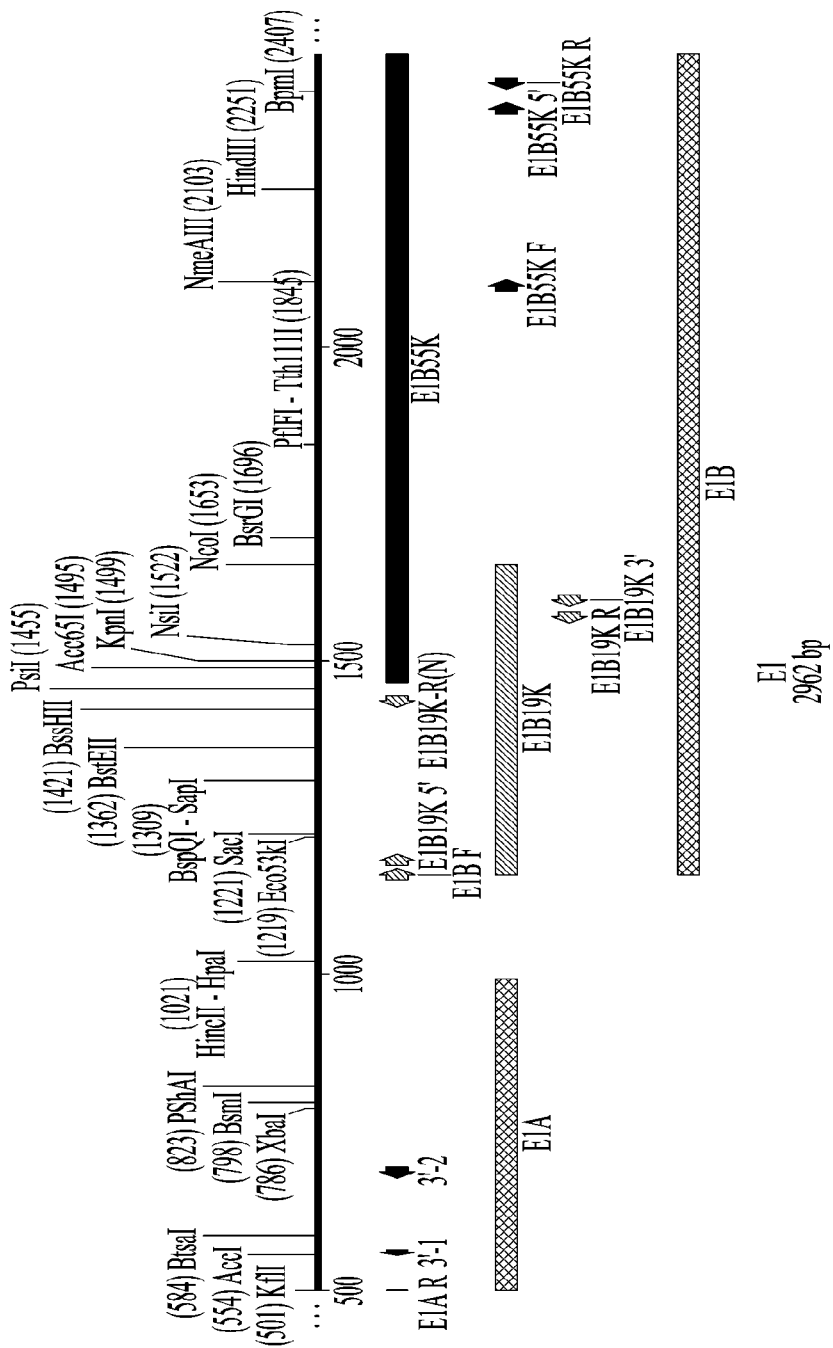
FIG. 1 is a schematic diagram of an adenoviral E1 gene used in the present invention.

The terms typically used in the present invention are defined as follows.

In the present invention, an adenoviral E1 has an adenoviral autoreplication capability.

The term "cell line" used in the present invention refers to a clone of cultured cells capable of carrying on a family line by continuously dividing and proliferating cells by means of cell culture, that is, a series of cell lineages whose genetic traits are preserved even when the cells are subcultured.

The term "promoter" used in the present invention refers to a regulatory sequence that is a nucleic acid sequence region in which transcription initiation and rate are regulated. Such a promoter may contain a genetic element which may bind to regulatory proteins and molecules such as RNA polymerases and other transcription factors to initiate specific transcription of a nucleic acid sequence. The terms "effectively aligned," "effectively bound," "under the control," and "under the transcriptional control" mean that a promoter is aligned at a proper position and/or orientation of action with regard to the nucleic acid sequence regulating transcription initiation and expression of the sequence.

The term "operably linked" used in the present invention means that one nucleic acid fragment is bound to another nucleic acid fragment so that the function or expression of the one nucleic acid fragment are affected by the another nucleic acid fragment. Also, an expression control sequence refers to a DNA sequence that regulates expression of an operably linked nucleic acid sequence in certain host cells. Such a control sequence includes any operator sequence for controlling the transcription, a sequence encoding a proper mRNA ribosome binding site, and a sequence for controlling termination of the transcription and reading.

The term "vector" used in the present invention refers to a DNA that transfers a genetic material from one cell to another. To construct the vector, a process of linking a desired DNA to another DNA should be performed. In this case, the DNA thus formed is referred to as a recombinant DNA.

The term "recombination" used in the present invention refers to a process of linking a DNA fragment of any organism to another DNA molecule. In the present invention, the resulting construct may be used as a recombinant vector or a recombinant virus.

The term "homologous recombination" used in the present invention refers to a strand exchange between two homologous DNA chains.

The term "introduction" used in the present invention means that a foreign DNA is allowed to flow in cells by means of transfection or transduction. The transfection may be performed using various methods known in the related art, such as calcium phosphate-DNA co-precipitation, DEAE-dextran-mediated transfection, polybrene-mediated transfection, electroporation, microinjection, liposome fusion, lipofectamine, and protoplast fusion. Also, the transduction is delivery of a gene into cells by means of infection using a virus or a viral vector particle.

The term "nucleic acid" used in the present invention refers to a polymeric material consisting of purine bases and pyrimidine bases/sugars/phosphate groups. In this case, the nucleic acid is a polymeric organic matter assembled from unit materials called nucleotides. A pentose sugar is a type of carbohydrate having 5 carbon atoms (hereinafter abbreviated as 'sugar'). Such sugars are divided into riboses and deoxyriboses. There are five bases: adenine (A), guanine (G), thymine (T), cytosine (C), and uracil (U).

The term "packaging system for producing a virus" used in the present invention refers to a system for producing a virus. In the present invention, the packaging system may be used to produce an adenovirus or a retrovirus. The packaging system for producing a virus includes nucleic acid molecules and proteins necessary for virus production.

The term "treatment" refers to an approach for obtaining beneficial or desirable clinical results. For the purpose of the present invention, the beneficial or desirable clinical results are non-limiting, and encompass relieving symptoms, reducing a range of diseases, stabilizing (i.e., not worsening) a disease status, delaying progression of a disease or reducing a progression rate of the disease, ameliorating or temporarily relieving and (partially or fully) mitigating a disease status, and determining whether the disease status is detectable or not.

The term "treatment" refers to both therapeutic and prophylactic treatments or measures. The treatments include treatments required for disorders to be prevented, as well as disorders which have been already developed. The term "palliating a disease" refers to reducing a range of the disease status and/or undesirable clinical signs and/or delaying or lengthening a time course of progression of the clinical signs, compared to when a subject undergoes no treatment.

The term "approximately" indicates an amount, level, value, number, frequency, percent, dimension, size, quantity, weight or length changed by 30%, 25%, 20%, 15%, 10%, 9%, 8%, 7%, 6%, 5%, 4%, 3%, 2%, or 1% from a reference amount, level, value, number, frequency, percent, dimension, size, quantity, weight or length.

Throughout this specification, it will be further understood that the terms "comprises," "comprising," "includes" and/or "including" specify the presence of stated steps or elements, and/or groups thereof, but do not preclude the presence or addition of one or more other steps or elements, and/or groups thereof, unless the context clearly indicates otherwise.

Hereinafter, the present invention will be described in detail.

The present invention provides a cell line for producing an adenovirus, which expresses an adenoviral E1 protein; and further expresses at least one of E1A and E1B proteins.

Also, the present invention provides a method of preparing a cell line for producing an adenovirus; and use of the cell line.

I. Cell Line

One aspect of the present invention is directed to a cell line having a virus-producing ability.

The term "virus-producing ability" refers to a state in which the virus-producing ability is increased, enhanced, or improved by artificially engineering (e.g., deleting) a certain factor (e.g., a gene, a protein, or the like) for the purpose of treating or preventing a disease in order to prevent a certain function (e.g., replication, transcription, translation, or the like) from being expressed.

The certain factor may be a gene associated with the self-replication of a virus.

The certain function may be a self-replication function of a virus.

The virus has a property of delivery of its own gene to another host in order to replicate and proliferate in the host. Such a virus may serve as a vector, which removes pathogenicity and delivers a treatable gene, using the property.

The cell line is a cell line having a virus-producing ability, which is derived from one or a combination of two or more selected from a retrovirus, an adenovirus, an adeno-associated virus (AAV), a lentivirus, a herpes simplex virus (HSV), and the like, but the present invention is not limited thereto.

The cell line may include normal cells, cancer cells, stem cells, immune cells, and the like, but the present invention is not limited thereto. Preferably, the cell line may be a normal cell line.

The cell line may include a human-derived cell line, a mouse-derived cell line, a pig-derived cell line, a monkey-derived cell line, a sheep-derived cell line, a plant-derived cell line, and the like, but the present invention is not limited thereto. Preferably, the cell line may be a human-derived cell line.

The cell line may include i) a first cell line including at least one E(refer to FIG. 1) gene; and ii) a second cell line transfected with the product obtained from the first cell line. The second cell line includes two or more E genes. Preferably, the second cell line includes all the E genes and E gene subtypes.

The product obtained from the first cell line may be a virus expressing at least one E gene.

The E gene may include one or more selected from E1, E2, E3, and E4 genes, and the like, but the present invention is not limited thereto. More particularly, the E gene may be an E1 gene. Preferably, the E gene may be an adenoviral E1 gene.

Some of the adenoviral E1, E2 and E4 genes are essential for the viral growth, and the E3 gene is not essential for the viral growth but has information on proteins evading an immune system of host cells.

The E gene may also include E gene subtypes.

The E gene subtypes may include one or more selected from E1A, E1B, E2A, E2B, E3A, E3B, E4A, E4B, and the like, but the present invention is not limited thereto. More particularly, the E gene subtypes may be E1A and E1B. Preferably, the E gene subtypes may be adenoviral E1A and E1B.

The E1B gene includes a nucleotide sequence (E1B19K) encoding E1B 19K and a nucleotide sequence (E1B55K) encoding E1B 55K, and inhibits an apoptosis signaling pathway.

It should be understood that the E genes described hereinafter are interpreted to also include the E gene subtypes.

The first cell line may include one or more selected from the E genes E1, E2, E3, E4, E1A, E1B, E2A, E2B, E3A, E3B, E4A, E4B, and the like, or a combination thereof, but the present invention is not limited thereto.

According to one embodiment, for example, the first cell line may include one or more genes selected from the E genes E1, E1A, and E1B.

According to one embodiment, the first cell line may be a cell line independently including each of the E genes E1, E1A, and E1B.

According to one embodiment, the first cell line may include E1; and E1A or E1B.

According to one embodiment, the first cell line may include E1, E1A, and E1B.

The product obtained from the first cell line may be a product obtained in the form of a virus by inserting the E gene into a vector. In this case, a non-viral vector or a viral vector may be used as the vector. More particularly, the vector may be a viral vector, preferably a retroviral vector.

According to one embodiment, the first cell line may be a product obtained from the first cell line by inserting each of the E1, E1A and E1B genes into a retroviral vector, thereby obtaining retroviruses including the E1, E1A and E1B genes, respectively.

According to one embodiment, the first cell line may be a product obtained from the first cell line by inserting the E1 and E1A or/and E1B gene into retroviral vectors, thereby obtaining retroviruses including the E1 and E1A or/and E1B genes.

The retroviral vector may be a non-replicating recombinant retroviral vector having no autoreplication capability.

According to one embodiment, the retroviral vector may include a foreign gene as a gene delivery vector.

Examples of the foreign gene include any genes to be expressed in target cells, for example, nucleic acids encoding polypeptides (enzymes, growth factors, cytokines, receptors, structural proteins, and the like), antisense RNA, ribozymes, decoys, RNAs causing RNA interference, and the like, but the present invention is not particularly limited thereto.

Also, a promoter, an enhancer, a terminator or other transcription regulatory elements may be inserted into the nucleic acids in order to control the expression of the foreign gene as described above. Also, the retroviral vector may have a proper marker gene (for example, a drug-resistant gene, a gene encoding a fluorescence protein, a gene encoding an enzyme capable of functioning as a reporter such as β-galactosidase, luciferase, or the like) enabling the selection of the gene-introduced cells.

The drug-resistant gene may be an antibiotic-resistant gene. According to one example of the present invention, the drug-resistant gene may be a gene resistant to ampicillin, gentamycin, carbenicillin, chloramphenicol, streptomycin, kanamycin, geneticin, neomycin, and tetracycline, but the present invention is not limited thereto.

According to one exemplary embodiment, the promoter may include a murine leukemia virus (MLU) long terminal repeat (LTR) promoter, a cytomegalovirus (CMV) promoter, an adenovirus early promoter, an adenovirus late promoter, a vaccinia virus 7.5K promoter, an SV40 promoter, an HSV tk promoter, a Rous sarcoma virus (RSV) promoter, an elongation factor-1 alpha (EF1 alpha) promoter, a metallothionein promoter, a beta-actin promoter, a promoter of a human IL-2 gene, a promoter of a human interferon gene, a promoter of a human interleukin-4 gene, a promoter of a human lymphotoxin gene, a promoter of a human granulocyte-macrophage colony-stimulating factor (GM-CSF) gene, a human phosphoglycerate kinase (PGK) promoter, or a mouse phosphoglycerate kinase (PGK) promoter, but the present invention is not limited thereto.

According to one exemplary embodiment, the promoter may be an elongation factor-1 alpha (EF1α) promoter.

The recombinant retroviral vector (hereinafter also referred to as a recombinant retrovirus) used in the present invention may be a retroviral vector known in the art.

For example, an MFG vector, an α-SGC vector (pamphlet of International Publication No. 92/07943), retroviral vectors such as pBabe [Nucleic Acids Research, Vol. 18, pp. 3587-3596 (1990)], pLXIN (Clontech Laboratories, Inc.), pDON-AI(Takara-Bio Inc.), a lentiviral vector [a human immunodeficiency virus (HIV)-derived vector, a simian immunodeficiency virus (SIV)-derived vector, or the like], a pBApo-EF1αNeo DNA (TaKaRa Code 3243) or pBApo-EF1αPur DNA (TaKaRa Code 3244) vector, or a modified vector thereof may be used.

According to one exemplary embodiment of the present invention, the retroviral vector may be an MLV-derived vector from which gag, pol and env genes are removed.

According to one embodiment, a retroviral vector including each of nucleic acid sequences encoding adenoviral E1, E1A, E1B proteins may be constructed.

According to one embodiment, the retroviral vector may further include an elongation factor-1 alpha (EF1a) promoter.

According to one embodiment, the retroviral vector may further include an LTR sequence.

According to one embodiment, the retroviral vector may further include an IRES neo sequence.

The obtaining of the product in the form of a virus may include packaging genes of a vector when a virus-producing cell line is transfected with the vector together with a packaging plasmid.

The transfection of the virus-producing cell line with the vector may be performed using various methods known in the related art.

According to one exemplary embodiment, the vector may be imported into cells using methods such as microinjection; calcium phosphate precipitation; electroporation; liposome-mediated transfection; DEAE-dextran treatment; and gene bombardment, but the present invention is not limited thereto.

The packaging plasmid has no cis-acting sequence essential for most of reverse transcription and integration, and is designed to express only gag, pol, and env viral proteins.

According to one exemplary embodiment of the present invention, the retrovirus packaging cell line transfected with the retroviral vector includes various cells.

Packaging cell lines known in the art, for example, PG13 (ATCC CRL-10686), PA317 (ATCC CRL-9078), GP+E-86 or GP+envAm-12 (U.S. Pat. No. 5,278,056), Psi-Crip [Proc. Natl. Acad. Sci. USA., Vol. 85, pp. 6460-6464 (1988)], and the like may be used as the retrovirus packaging cell line as described above, but the present invention is not limited thereto.

According to one exemplary embodiment of the present invention, retrovirus-producing cells may be prepared by introducing a packaging plasmid (a retrovirus packaging kit; disclosed in Korean Patent No. 10-1362111; TAKARA-BIO Inc., and the like) loaded with genes necessary for production of retroviral particles into 293 cells or 293T cells.

According to one exemplary embodiment of the present invention, the retrovirus packaging cell line may be a human-derived cell line. According to a preferred exemplary embodiment of the present invention, the retrovirus packaging cell line may be an L132 cell line.

The first cell line may produce a virus expressing the E gene. Preferably, the first cell line may produce a retrovirus.

The retrovirus is characterized in that the retrovirus is effective for transfecting the adenovirus-producing cell line because the retrovirus may serve to stably insert an adenoviral E1 gene and also has a high titer.

According to the present invention, a cell line is transfected with the prepared recombinant retrovirus to obtain a cell line expressing the adenoviral E1 gene.

The second cell line may be a cell line infected with a virus produced by the first cell line. More particularly, the second cell line may be a cell line obtained by transfecting an adenovirus-producing cell line with the first cell line, followed by transfection with an adenoviral vector. In this case, the second cell line may include two or more E genes.

Hereinafter, types of E genes that may include the second cell line are described by way of example, but the present invention is not limited thereto.

According to one embodiment, when the first cell line independently includes each of E1, E1A, and E1B, the second cell line may be a cell line obtained by transfecting an adenovirus-producing cell line with two or more of the viruses obtained from the first cell line in a simultaneous or sequentially.

According to one embodiment, the second cell line may be a second cell line infected with the E1 product of the first cell line and the E1A product of the first cell line. Also, the second cell line may be a cell line infected with the E1 product of the first cell line and the E1B product of the first cell line. Also, the second cell line may be a cell line infected with the E1 product of the first cell line, the E1A product of the first cell line, and the E1B product of the first cell line.

According to one embodiment, the second cell line may be a second cell line which is first transfected with the E1 product of the first cell line, followed by infection with the E1A product of the first cell line. Also, the second cell line may be a second cell line which is first transfected with the E1 product of the first cell line, followed by infection with the E1B product of the first cell line. Also, the second cell line may be a cell line which is first transfected with the E1 product of the first cell line, followed by transfection with the E1A product of the first cell line and the E1B product of the first cell line.

That is, the second cell line may be a cell line which is transfected with the products of the first cell line in a desired order or combination. Preferably, the second cell line may be a cell line which is first transfected with the E1 product of the first cell line, followed by infection with the E1A or E1B product of the first cell line.

According to one embodiment of the present invention, the second cell line is a cell line obtained by transfecting an adenovirus-producing cell line with an E1 retrovirus.

According to another embodiment of the present invention, the second cell line is a cell line obtained by first transfecting an adenovirus-producing cell line with an E1 retrovirus, followed by further transfection with an E1A retrovirus.

The transfection is as described above.

The second cell line may further include an adenoviral vector.

The adenoviral vector may further include an enhancer, a terminator or other transcription regulatory elements for controlling the expression of a foreign gene. According to another exemplary embodiment of the present invention, the adenoviral vector may further include a marker gene. The marker gene may be a drug-resistant gene, a gene encoding a fluorescence protein, a gene encoding an enzyme capable of functioning as a reporter such as β-galactosidase or luciferase, and the like, but the present invention is not limited thereto.

A cell line expressing an adenoviral E1 protein may be transfected with the adenoviral vector of the present invention. A method of introducing the adenoviral vector may be performed using various methods known in the related art.

According to one exemplary embodiment of the present invention, the vector may be imported into cells using methods such as microinjection; calcium phosphate precipitation; electroporation; liposome-mediated transfection; DEAE-dextran treatment; and gene bombardment, but the present invention is not limited thereto.

The adenoviral vector of the present invention may enable the production of an RNA transcript from the adenoviral vector, and the transcript may be packaged into an adenovirus, which is then excreted into a medium.

Therefore, the adenovirus according to the present invention may be obtained by collecting and concentrating the medium.

According to one exemplary embodiment of the present invention, the adenovirus obtained by collection and concentration of the medium may further undergo a purification process for clinical applications, which may be carried out using methods known in the art.

According to one exemplary embodiment of the present invention, the purification of the adenovirus may be performed using methods such as differential centrifugation, density-gradient centrifugation, column chromatography, expanded chromatography, virus precipitation, contaminant modification, and cell component breakdown using an enzyme, but the present invention is not limited thereto.

The first cell line and the second cell line are cell lines having different virus-producing abilities. Particularly, the first cell line may be a cell line having a retrovirus-producing ability, and the second cell line may be a cell line having an adenovirus-producing ability.

The retrovirus is considered to be a vector most useful for stably inserting a therapeutic gene into an RNA virus. However, the retrovirus may be inserted into only dividing cells, and the therapeutic gene may not be imported into non-dividing cells. Also, the retrovirus has drawbacks in that a replication competent retrovirus (RCR) showing partial replicability may be generated, and the retrovirus may be inactivated by serum complements.

The adenovirus is in the form of double-stranded DNA, and thus shows a high expression level in both dividing and non-dividing cells. Also, a recombinant virus having good stability and a high titer may be produced. However, the adenoviruses may be isolated from various organisms spanning from algae to humans, and may be divided into six subgenes, depending on their structural, biochemical, and immunological characteristics. Ad2 and Ad5 have been widely used as the adenoviral vector used for gene therapy so far. However, when there is a replication competent adenovirus (RCA), a gene delivery vector should be used to minimize production of the RCA because the RCA may cause severe side effects in an immunodeficient patient.

The adenovirus type 5 has a replication origin essential for virus replication, and includes E1, E2, E3, and E4 genes, and genes encoding a viral capsid protein.

The E gene and the E gene subtypes are genes associated with the replication competent adenovirus (RCA).

The RCA refers to an adenovirus in which a viral vector included in the first cell line and the second cell line is self-replicating when the first cell line and the second cell line are applied as a delivery tool for gene therapy. In this case, when the RCA is produced, side effects may be caused in patients deficient in an immune response.

The cell line may be a cell line having a low RCA-producing probability and an improved adenovirus-producing ability.

Figure 11:
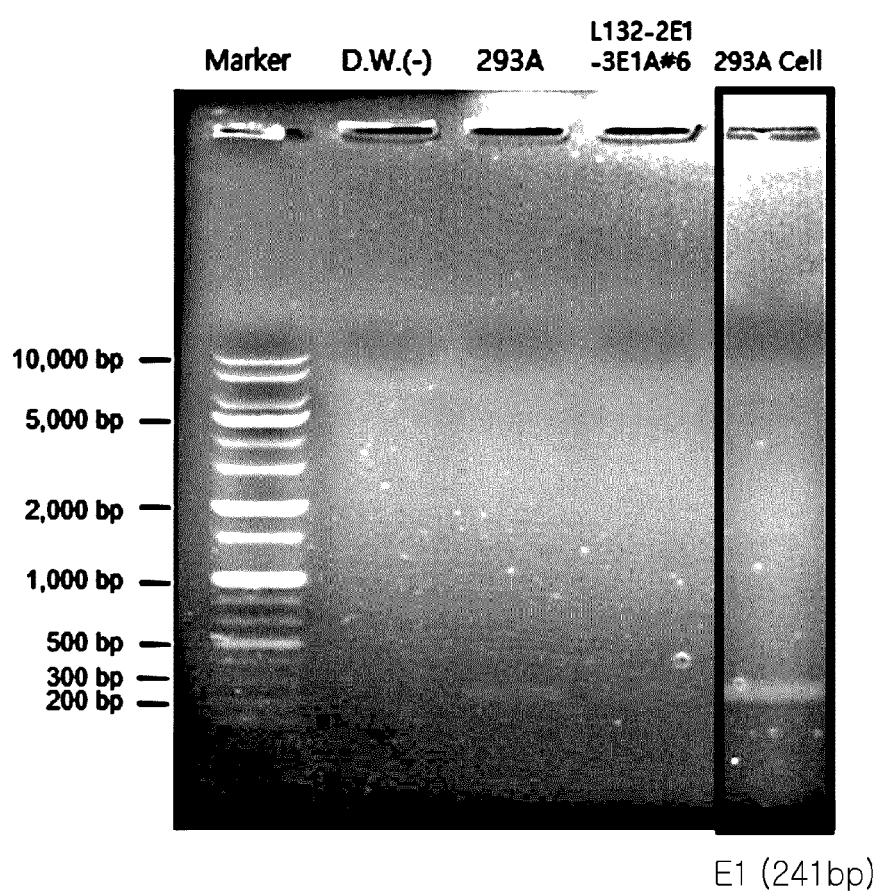
FIG. 11 shows the results of verifying an RCA test on the cell line for producing an adenovirus, in which L132 cells were transfected with an E1 retrovirus, followed by additional transfection with an E1A retrovirus.

According to some embodiments of the present invention, the result of RCA reactivity experiments on the cell lines having an adenovirus-producing ability, which are obtained by transfecting an adenovirus cell line with the E1 and E1A or/and E1B retroviruses, shows that the RCA reactivity of the adenovirus cell line may be confirmed by formation of an E1 band, as shown in FIG. 11.

The adenovirus produced by the cell line for producing an adenovirus according to the present invention may not have an E1 region therein, thereby reducing an immune response caused by the autoreplication capability of the adenovirus when the adenovirus is used as a gene therapeutic agent, and the like.

Also, the cell line for producing an adenovirus according to the present invention has a characteristic of not producing the replication competent adenovirus (RCA) because the cell line of the present invention does not have the same sequence as the adenovirus-producing vector, thereby producing an adenovirus that can be used for gene therapy, and the like.

The cell line according to the present invention is a cell line for producing an adenovirus, which has an enhanced adenovirus-producing ability.

The cell line may be a cell line producing the adenovirus. Preferably, the cell line may be a cell line producing the adenoviral E1 gene.

The cell line producing the E1 gene may be screened by measuring cell viability.

The cell line producing the adenoviral E1 gene may include various cells. According to one exemplary embodiment of the present invention, the cell line producing the adenoviral E1 gene may include carcinomic human alveolar basal epithelial cells (A549), human embryonic retinoblasts (HER), human cervical cancer cells (HeLa), Chinese hamster ovary cells (CHO), baby hamster kidney cells (BHK), mouse embryonic fibroblast cells (3T3), myeloma cells, rat pheochromocytoma cells (PC12), human amniocytes, human dermal fibroblasts (WS1), human lung fibroblasts (MRCS), human lung fibroblast cells (W138), or human lung cells (L132), but the present invention is not limited thereto.

According to one specific embodiment of the present invention, the cell line may be a cell line having an adenovirus-producing ability, which is obtained by introducing an E1 gene into the L132 cell line.

According to another specific embodiment of the present invention, the cell line may be a cell line having an adenovirus-producing ability, which is obtained by introducing an E1 gene into the L132 cell line to improve stability, followed by introduction of an E1A or/and E1B gene.

Therefore, the cell line of the present invention may provide the adenoviral E1 gene with high stability to cross-complement an E1-deleted adenovirus, and thus may provide a cell line capable of producing an adenovirus with high efficiency.

II. Method of Producing Cell Line

Another aspect of the present invention is directed to a method of producing a cell line.

One exemplary embodiment of the method of producing a cell line may include a first step of obtaining a first cell line and second step of preparing a second cell line.

The method of producing a cell line is a method of transfecting a cell line with the product obtained from the first cell line to prepare the second cell line.

Hereinafter, the respective steps will be described.

The first step is to obtain a first cell line.

To obtain a first cell line including at least one E gene, the first step may include inserting the E gene; and producing an intermediate for producing a second cell line.

The inserting of the E gene includes inserting a gene sequence into an expression construct (vector) expressing the E gene. One or more selected from a lentiviral vector, an adenoviral vector, a retroviral vector, and the like may be used as the expression construct, but the present invention is not limited thereto. Preferably, the expression construct may be a retroviral vector.

The retroviral vector is as described above.

The insertion of the E gene into the expression construct will be described below with reference to examples, but the present invention is not limited thereto.

According to one exemplary embodiment, two or more genes selected from E1, E1A, and E1B may be inserted to be prepare: a retroviral vector including the E1 and E1A genes, a retroviral vector including the E1 and E1B genes, a retroviral vector including the E1A and E1B genes, and a retroviral vector including the E1, E1A and E1B genes. According to one exemplary embodiment, all three of the E1, E1A, E1B genes may be inserted to prepare a retroviral vector including the E1, E1A and E1B genes.

The order of insertion of the two or three genes may vary depending on a purpose.

Preferably, the E1, E1A, and E1B genes may be inserted to prepare an E1 retroviral vector, an E1A retroviral vector, and an E1B retroviral vector, respectively.

Figure 10:
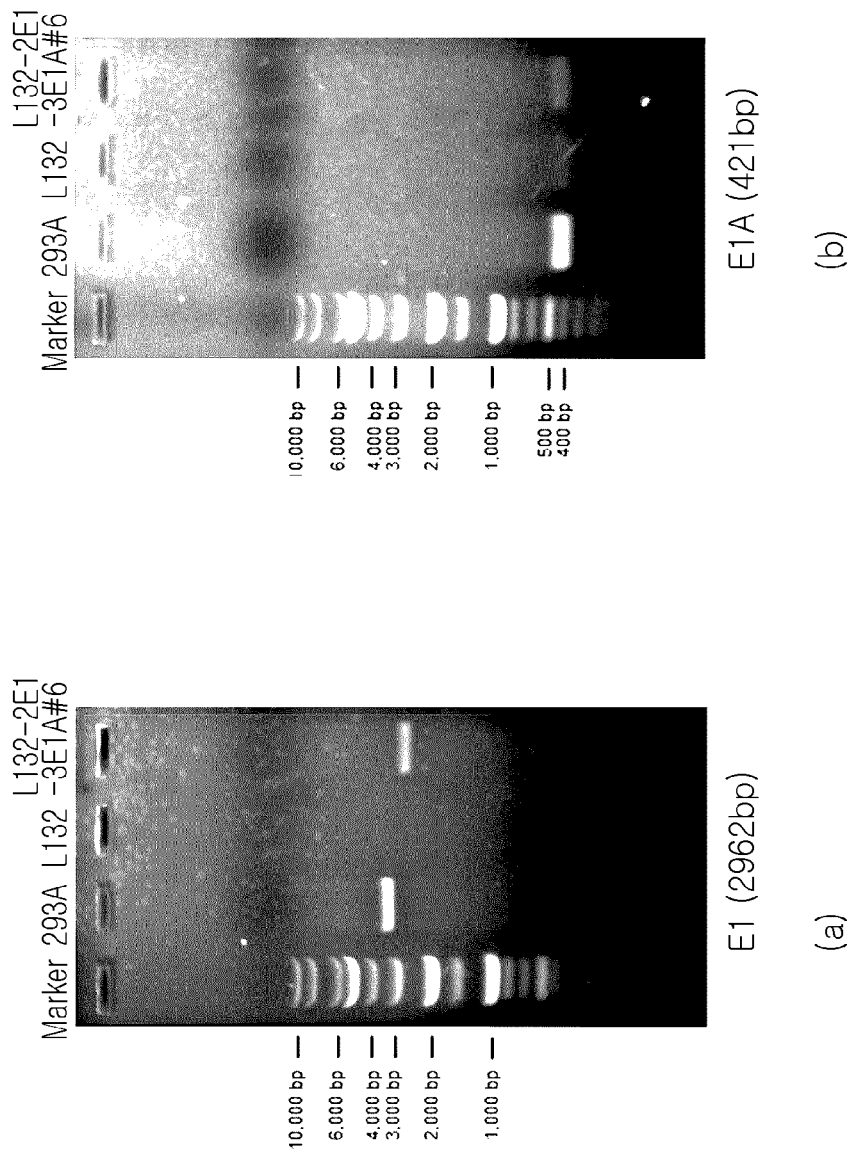
FIG. 10 shows the results of determining whether the E1 and E1A genes were transduced in a cell line for producing an adenovirus, in which L132 cells were transfected with an E1 retrovirus, followed by additional transfection with an E1A retrovirus.

According to some embodiments of the present invention, the insertion of the E1 gene into the retroviral vector may be confirmed by determining whether the gene is inserted into the vector by means of PCR, as shown in FIG. 10.

Figure 6:
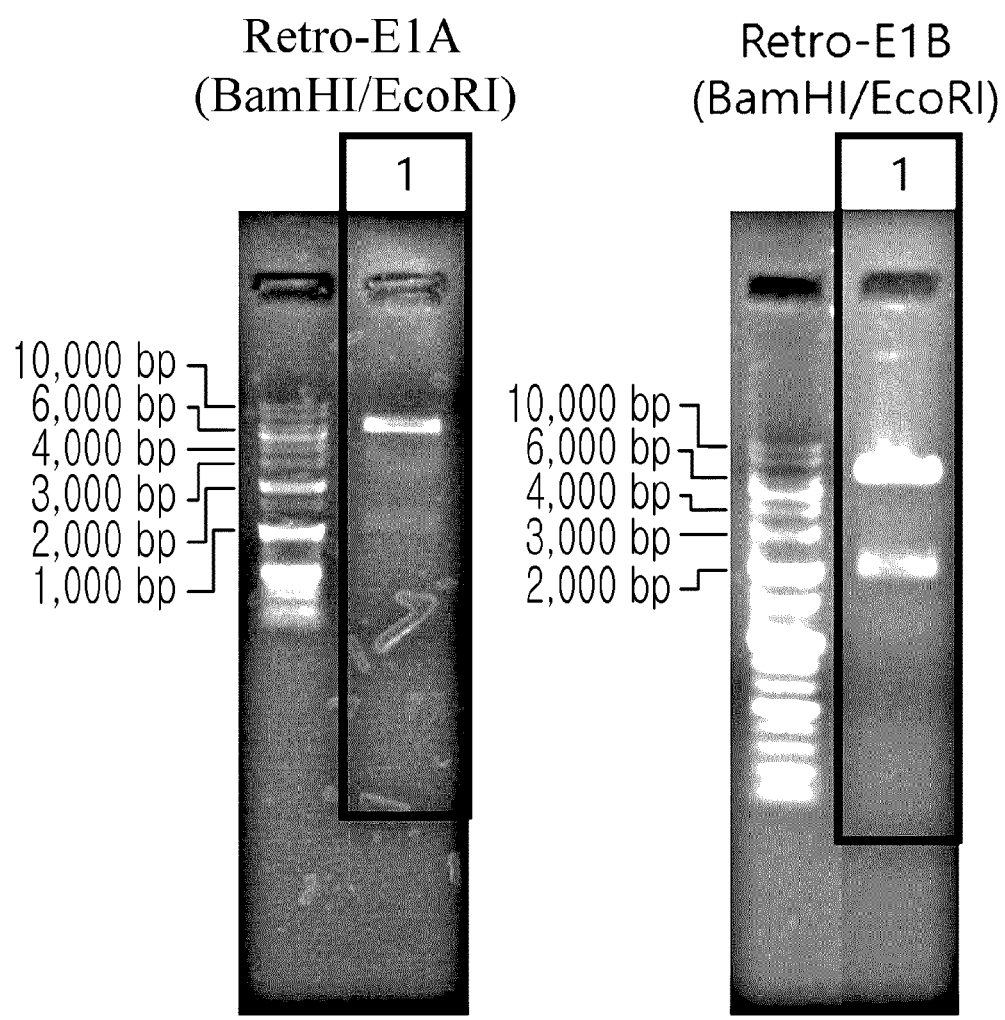
FIG. 6 shows the results of verifying that the E1A and E1B genes transduced in the cell line were transfected with the retroviral vector.

According to some embodiments of the present invention, the insertion of the E1A or E1B gene into the retroviral vector may be confirmed by determining whether the gene is inserted into the vector by means of PCR, as shown in FIG. 6 and FIG. 10.

The producing of the intermediate includes introducing the vector into which the E gene is inserted into proper cells to obtain the intermediate in the form of a virus. More particularly, a retrovirus-producing packaging cell line is transfected with the E gene-inserted retroviral vector together with a packaging plasmid to harvest a retrovirus.

When the retrovirus-producing cell line is transfected with the retroviral vector together with the packaging plasmid, genes of the retroviral vector may be packaged to produce the retrovirus. The transfection method is as described above.

The retrovirus-producing cell line is transfected with the retroviral vector together with the packaging plasmid, and cultured under conditions enabling the retrovirus production. The transfected cells are cultured for a predetermined time until the transfected cells form colonies to screen clones of the cell line. The screening of the clones may be performed using all methods known in the related art, such as a method of culturing a cell line, into which the retrovirus is introduced, in a medium, adding a select agent (for example, an antibiotic) to the medium, and collecting and sorting the cells resistant to the select agent or screening the cells resistant to the select agent as clones.

According to one embodiment, the retrovirus may be produced by transducing cells with a retroviral vector and gag-pol- and env-expressing plasmids at the same time, and concentrating and purifying only a supernatant of the cells after a predetermined time.

According to some embodiments of the present invention, the retrovirus is characterized in that the retrovirus is effective for transfecting the adenovirus-producing cell line because the retrovirus may serve to stably insert the adenoviral E1 gene and also has a high titer.

According to one exemplary embodiment of the present invention, the retrovirus including a nucleic acid sequence encoding the adenoviral E1 protein is prepared to prepare a cell line expressing the E1 protein for producing an adenovirus, which is used for gene therapy.

When the adenovirus-producing cell line is infected with the produced retrovirus, only a structure of the retroviral vector may be inserted into a chromosome of the cell line, thereby inducing expression of the adenoviral E1 protein which is encoded by a foreign gene.

The second step is to obtain a second cell line.

To obtain a second cell line including two or more E genes, the second step may include transfecting proper cells with the product of the first step to obtain the second cell line.

As described above, the second cell line is a cell line including two or more E genes. According to one exemplary embodiment, the second cell line is an adenovirus-producing cell line including one E gene and one E subtype gene.

The second step includes transfecting an adenovirus-producing cell with the retrovirus produced from the first cell line, followed by transfection with an adenoviral vector.

The transfection method is as described above.

According to one embodiment, the second cell line may be made by preparing a retrovirus including a nucleic acid sequence of one of E1, E1A, and E1B genes; obtaining each of the constructed retroviral vectors as the retrovirus; and transfecting a cell line for producing an adenovirus with the retrovirus.

According to one embodiment, the second cell line may be made by constructing retroviral vectors including nucleic acid sequences of each of E1, E1A and E1B genes; obtaining each of the constructed retroviral vectors as the retrovirus; and transfecting a cell line for producing an adenovirus with the E1 retrovirus, the E1A retrovirus, and the E1B retrovirus.

According to one embodiment, the second cell line may be made by constructing each of retroviral vectors including nucleic acid sequences of E1, E1A and E1B genes; obtaining each of the constructed retroviral vectors as the retrovirus; and transfecting a cell line for producing an adenovirus with the E1 retrovirus, the E1A retrovirus, and the E1B retrovirus.

According to one embodiment, the second cell line may be made by constructing retroviral vectors including nucleic acid sequences of two of E1, E1A, and E1B genes; obtaining each of the constructed retroviral vectors as the retrovirus; transfecting a cell line for producing an adenovirus with the retrovirus; and further infecting the cell line for producing an adenovirus, which has been transfected with the retrovirus including the two nucleic acid sequences, with the retrovirus including the other one nucleic acid sequence.

According to one embodiment, the second cell line may be made by constructing retroviral vectors including nucleic acid sequences of each of E1, E1A and E1B genes; obtaining each of the constructed retroviral vectors as the retrovirus; transfecting a cell line for producing an adenovirus with the E1 retrovirus; and further infecting the cell line for producing an adenovirus, which has been transfected with the E1 retrovirus, with the E1A and/or E1B retrovirus.

According to one embodiment of the present invention, the adenovirus-producing efficiency of the cell line producing the adenoviral E1 gene may be confirmed by means of real-time PCR by measuring a titer of the cell line to determine how much the cell line produces the adenovirus, as shown in FIG. 7, FIG. 8, FIG. 9, and FIG. 12.

Figure 7:
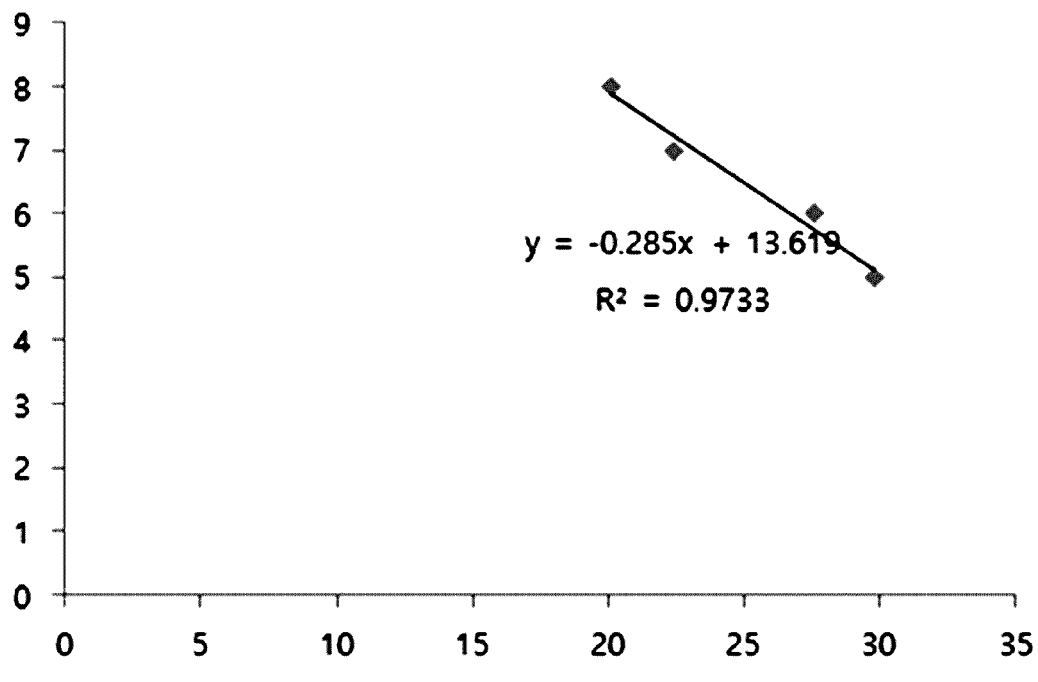
FIG. 7 shows the results of measuring the titer of adenovirus produced when L132 cells were transfected with a retrovirus including the E1 gene.
Figure 8:
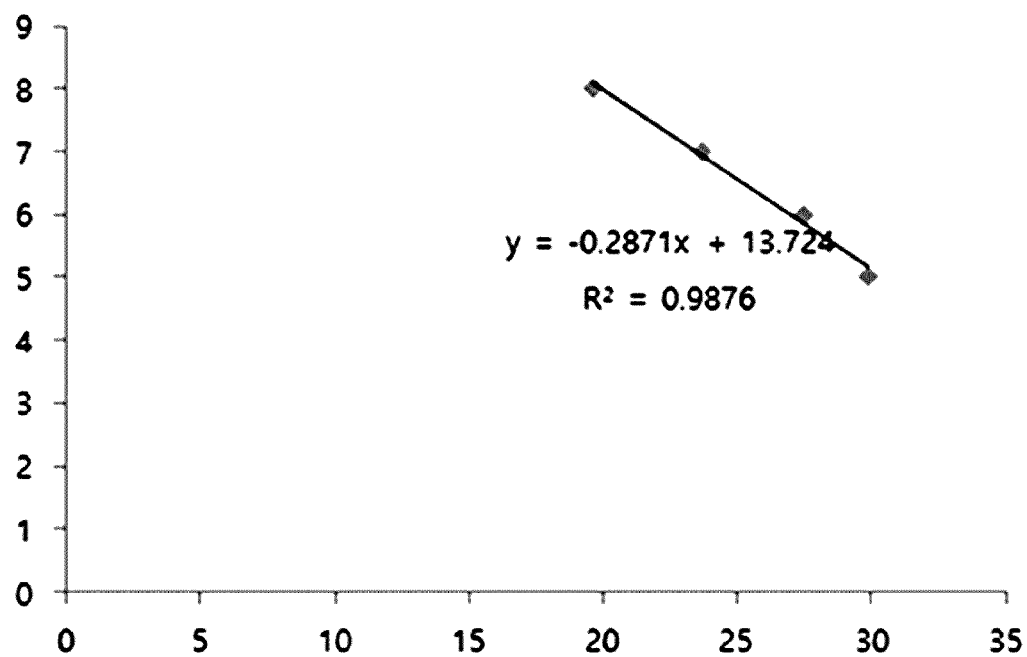
FIG. 8 shows the results of measuring the titer of adenovirus produced when L132 cells were transfected with a retrovirus including the E1 gene, followed by additional transfection with a retrovirus including the E1A gene.
Figure 9:
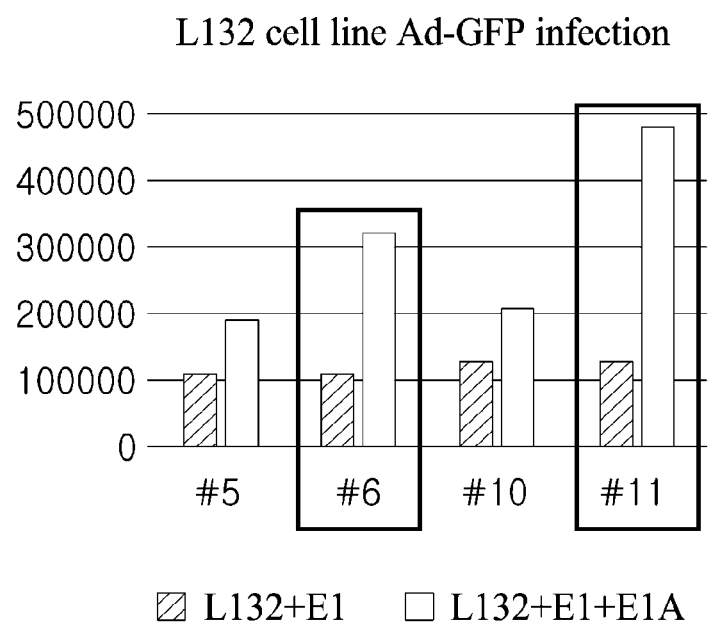
FIG. 9 shows the results of comparing the titer of adenovirus produced when L132 cells were transfected with an E1 retrovirus and when L132 cells were transfected with a retrovirus including the E1 gene, followed by additional transfection with a retrovirus including the E1A gene.

According to another embodiment of the present invention, it can be seen that the adenovirus-producing cell line transfected with the E1 retrovirus followed by transfection with the E1A or/and E1B retrovirus has a higher amount of produced adenovirus, compared to the adenovirus-producing cell line transfected with the E1 retrovirus, as shown in FIG. 7, FIG. 8, and FIG. 9.

According to another embodiment of the present invention, it can be seen that the adenovirus-producing cell line transfected with the E1 retrovirus followed by transfection with the E1A or/and E1B retrovirus has no RCA reaction, as shown in FIG. 11.

When the method of producing a cell line described above is used, a cell line capable of producing the adenovirus may be prepared. In this case, the cell line capable of producing the adenovirus may be a cell line derived from human cells, but the present invention is not limited thereto. Preferably, the cell line derived from human cells may be an L132 cell line.

Additionally, the adenovirus according to the present invention may be obtained by collecting and concentrating the medium as described above.

According to one exemplary embodiment of the present invention, the adenovirus obtained by collection and concentration of the medium may further undergo a purification process for clinical applications, which may be carried out using methods known in the art.

According to one exemplary embodiment of the present invention, the purification of the adenovirus may be performed using methods such as differential centrifugation, density-gradient centrifugation, column chromatography, expanded chromatography, virus precipitation, contaminant modification, and cell component breakdown using an enzyme, but the present invention is not limited thereto.

The adenovirus produced from the cell line of the present invention has a reduced autoreplication capability. The reduced autoreplication capability of the adenovirus produced from the cell line of the present invention may be confirmed by amplifying an adenoviral genome present in a culture supernatant of the cell line of the present invention using a polymerase chain reaction (PCR) to analyze whether an E1 region exists in the adenoviral genome.

The adenovirus produced from the cell line for producing an adenovirus according to the present invention may not have an E1 region, and thus may have a reduced autoreplication capability, thereby reducing an immune response caused by the autoreplication capability of the adenovirus when the adenovirus is used as a gene therapeutic agent, and the like.

Also, because the cell line for producing an adenovirus according to the present invention does not have the same sequence as the adenovirus-producing vector, the cell line is characterized in that no replication competent adenovirus (RCA) is produced, thereby producing the adenovirus capable of being used for gene therapy, and the like.

The cell line prepared by the method of the present invention is a cell line for producing an adenovirus having a reduced autoreplication capability, which has an improved adenovirus-producing ability.

III. Use of Cell Line

Packaging System for Producing AAV

The adenovirus produced from the adenovirus-producing cell line of the present invention may be used to produce an adeno-associated virus.

The adeno-associated virus (AAV) of the present invention has an ability to effectively infect various cells (muscle, brain, lung, retina, liver, ear, heart, blood vessel, and the like) and is inserted into a chromosome of a target cell to stably express a therapeutic protein for a long period of time.

According to one exemplary embodiment of the present invention, the adenovirus obtained by the cell line for producing an adenovirus; a cell line including a nucleic acid sequence encoding a rep protein of an adeno-associated virus (AAV) and a nucleic acid sequence encoding a cap protein of the AAV; and a packaging system for producing the AAV, which includes an AAV vector, may be provided.

According to one exemplary embodiment of the present invention, the nucleic acid sequence encoding the rep protein of the adeno-associated virus (AAV) and the nucleic acid sequence encoding the cap protein of the AAV may be introduced into the cell line using methods known in the art.

In this case, a method of introducing the nucleic acid sequence into the AAV-producing cell line may include methods such as calcium phosphate precipitation, lipofection, DEAE dextran treatment, polyethylene imine treatment, electroporation, and the like, but the present invention is not limited thereto.

Also, the introduction of the nucleic acid into the AAV-producing cell line may be performed using a vector or a plasmid, and the vector may include a retroviral vector, a lentiviral vector, an adenoviral vector, and the like, but the present invention is not limited thereto.

According to one exemplary embodiment of the present invention, the AAV vector may be constructed using methods known in the related art.

According to one exemplary embodiment of the present invention, the vector may be imported into the cells using methods such as microinjection; calcium phosphate precipitation; electroporation; liposome-mediated transfection; DEAE-dextran treatment; and gene bombardment, but the present invention is not limited thereto.

The AAV obtained by the aforementioned packaging system for producing AAV may be used for gene therapy because the AAV shows efficient infection ability and is stably inserted into a target cell.

Gene Therapeutic Agent

A gene therapeutic agent may be prepared using the adenoviruses produced by the prepared cell line for producing an adenovirus and the packaging system for producing an adenovirus having a reduced autoreplication capability.

The gene therapy of the present invention is a method of treating a congenital or acquired genetic disorder, which is difficult to treat using conventional methods, using a genetic engineering method.

According to one exemplary embodiment of the present invention, a therapeutic method of administering a genetic material such as DNA and RNA into the human body to express a therapeutic protein or inhibit expression of a certain protein in order to treat and prevent a chronic disease such as congenital or acquired genetic defects, viral diseases, cancers, or cardiovascular diseases may be provided as the gene therapy.

According to one exemplary embodiment of the present invention, the adenovirus may include a target gene necessary for gene therapy to deliver the target gene in vivo.

According to another exemplary embodiment of the present invention, the adenovirus may deliver the target gene into cells collected from a patient.

According to still another exemplary embodiment of the present invention, the adenovirus may include a target gene instead of the E1 gene.

According to one exemplary embodiment of the present invention, the adenovirus may include a target gene instead of the E1 gene.

When the adenovirus obtained from the cell line for producing an adenovirus having a reduced autoreplication capability according to the present invention is used for gene therapy, the adenovirus has advantages in that the adenovirus may reduce an immune response due to the reduced autoreplication capability, and has no risk of RCA production.

Antibody-Producing Cell Line

The cell line for producing an adenovirus having a reduced autoreplication capability according to the present invention may be used to produce an antibody.

For production of a therapeutic antibody using the cell line, one important step is to screen a cell line having high productivity.

The adenoviral E1 gene of the present invention may be endowed with high productivity by means of immortalization, that is, persistent cell division.

Because the adenoviral E1A gene of the present invention is associated with the permanent cell division and the E1B gene has an ability to inhibit cell death (i.e., apoptosis), when a recombinant cell line is constructed by transfecting a cell line with an E1 gene to express the E1 gene, followed by further transfection with an E1A or E1B gene to express the E1A or E1B gene as in the present invention, it is possible to obtain a cell line having high productivity.

In the present invention, an antibody is a specific protein molecule directed against an antigenic site. For the purpose of the present invention, the antibody is produced by the cell line of the present invention, and is an antibody that specifically binds to an antigen. In this case, the term "antibody" includes all of polyclonal antibodies, monoclonal antibodies, and recombinant antibodies.

According to one exemplary embodiment of the present invention, the polyclonal antibody using the cell line may be produced using methods widely used in the related art. In this case, the polyclonal antibody may be prepared from any animal hosts such as a goat, a rabbit, a sheep, a monkey, a horse, a pig, cattle, a dog, and the like, but the present invention is not limited thereto.

According to one exemplary embodiment of the present invention, the monoclonal antibody using the cell line may be prepared using a hybridoma method widely known in the related art (see Kohler and Milstein (1976) European Journal of Immunology 6: 511-519), or a phage antibody library technique (Clackson et al., Nature, 352: 624-628, 1991; Marks et al., J. Mol. Biol., 222: 58, 1-597, 1991).

According to one exemplary embodiment of the present invention, the antibody produced by the cell line may be isolated and purified using methods such as gel electrophoresis, dialysis, salt precipitation, ion exchange chromatography, affinity chromatography, and the like.

The produced antibody includes a complete antibody form having two full-length light chains and two full-length heavy chain as well as functional fragments of the antibody molecule. The functional fragments of the antibody molecule refers to fragments that retain at least an antigen-binding function, and include Fab, F(ab'), F(ab') 2, Fv, and the like.

According to one exemplary embodiment of the present invention, a human cell line may be used as an antibody-producing cell line, but the present invention is not limited thereto.

According to one exemplary embodiment of the present invention, a CHO cell line may be used as an antibody- and protein-producing cell line.

Because the antibody-producing cell line of the present invention does not have a morphological difference in glycosylation, the antibody-producing cell line has a characteristic of very low immunogenicity. Therefore, the antibody produced by the cell line may be effectively used as a therapeutic agent.

Production of Vaccine

The adenovirus-producing cell line of the present invention may be used as a vaccine-producing cell line.

Like in the antibody-producing cell line, high productivity is also important in the vaccine-producing cell line.

Therefore, in the present invention, a recombinant cell line may be constructed by transfecting a cell line with an E1 gene to express the E1 gene, followed by further transfection with an E1A or E1B gene to express the E1A or E1B gene, thereby obtaining a cell line having high productivity.

According to one exemplary embodiment of the present invention, a chicken egg or canine cells may be used to produce an influenza vaccine.

The vaccine produced according to the present invention may be properly formulated with a pharmaceutically available carrier. Therefore, the vaccine may be used to prepare a medical or pharmaceutical composition, and may be formulated into a solution for parenteral administration or a freeze-dried powder. The powder may be reconstituted before use by adding a suitable diluent or other pharmaceutically available carriers thereto. A liquid formulation may be a buffer solution, an isotonic solution, or an aqueous solution. The powder may be sprayed in an anhydrous form. Examples of the suitable diluent generally include isotonic saline, a standard 5% dextrose solution in water, or a buffered sodium or ammonium acetate solution. The formulation is particularly suitable for parenteral administration, and may also be used for oral administration or may be contained in a metered dose inhaler or a sprayer. Excipients, for example, polyvinyl pyrrolidone, gelatin, hydroxy cellulose, acacia, polyethylene glycol, mannitol, sodium chloride, sodium citrate, and the like may be preferably added.

The vaccine produced by the cell line of the present invention may be prepared for oral administration. A pharmaceutically available solid or liquid carrier may be added to improve or stabilize a composition. The solid carrier includes starch, lactose, calcium sulfate dihydrate, white clay, magnesium stearate or stearic acid, talc, pectin, acacia, agar, or gelatin. The liquid carrier includes syrup, peanut oil, olive oil, saline, or water. Also, the carrier may include a delayed release material (for example, glyceryl monostearate or glyceryl distearate) alone or in combination with a wax. An amount of the solid carrier may vary, and may preferably be in a range of approximately 20 mg to approximately 1 g per unit dose. When the liquid carrier is used, the formulation may be in the form of a syrup, an elixir, an emulsion, or an aqueous or non-aqueous suspension.

The vaccine produced by the cell line of the present invention may be formulated into forms including a medically available drug or a biological agent.

Also, the vaccine produced by the cell line of the present invention may be administered together with other drugs or biological agents useful for treatment of a targeted disease or symptoms thereof.

When the cell line according to the present invention is used to produce a vaccine, the cell line has low immunogenicity, thereby producing a safe vaccine.

EXAMPLES

Hereinafter, the present invention will be described in further detail with reference to examples thereof. However, it should be understood that the following examples are given for the purpose of illustration of the present invention only, and are not intended to limit the scope of the present invention, as will be apparent to those skilled in the art.

Example 1: Cloning of E1, E1A and E1B and Preparation of Retrovirus 1-1: Cloning of E1, E1A and E1B Genes into Retroviral Vector PCR was performed for an E1 gene (2,962 bp) of adenovirus type 5 as a template and an E1A gene (998 bp) and an E1B gene (1,808 bp) to obtain an E1A band of approximately 1 Kb and an E1B band of approximately 1.8 Kb.

A gene was cloned into a pGEM-T easy vector, and then sequenced to confirm DNA sequences of the E1A and E1B genes (see SEQ ID NO: 1 shown in FIG. 2 and SEQ ID NO: 2 shown in FIG. 3)

Figure 4:
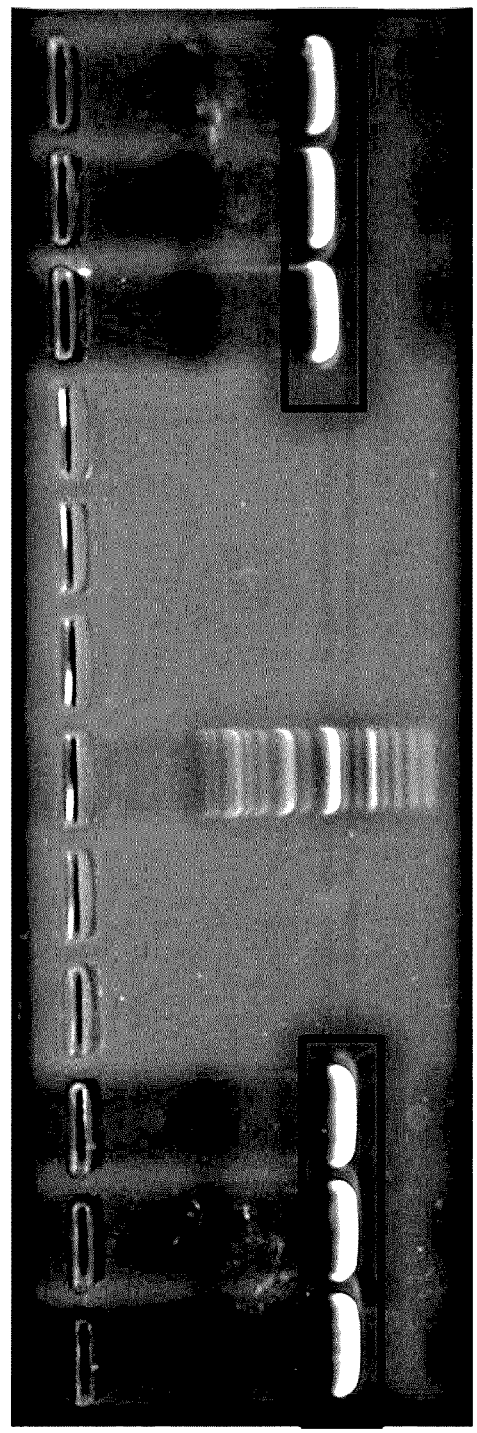
FIG. 4 shows the PCR results of the E1A gene used in the present invention.

Referring FIG. 4, it can be seen that the E1A gene was obtained by PCR using the specific primers.

In the clones whose DNA sequences were identified in the various clones, each of the E1, E1A, E1B, pro-E1, pro-E1A, and pro-E1B genes was cloned into a retroviral vector by means of enzyme digestion.

1-2: Production of Retrovirus

A packaging cell line expressing a gag-pol protein was co-transfected with the retroviral vector into which the gene was inserted together with a plasmid expressing a surface protein (an envelope), and then cultured for 3 days to obtain a supernatant. The supernatant was concentrated and purified using a centrifuge to produce the constructed retrovirus.

1-3: Confirmation of Retrovirus Production

To measure a titer using real-time PCR, a standard solution was serially diluted from 109 to 105 and used in consideration of the concentration and size of the vector plasmid DNA. For evaluation of optimal multiplicity of infection (MOD, cells were transfected with a control virus expressing GFP at a density of 1, 10, and 100, and an expression level of GFP was observed using a fluorescence microscope. From these results, it can be seen that the retrovirus was produced.

1-4: Confirmation of Introduction of E1, E1A and E1B Genes

To verify whether the E1 gene of Example 1-1 was expressed, mRNA expression was confirmed using RT-PCR. Introduction of the E1 gene was checked by measuring the E1A gene in which the shapes of mRNA and gDNA were distinguished by PCR because introns were included in the E1 gene.

The E1 gene was inserted into a retroviral vector, and HT1080 cells were transfected with the retroviral vector using JetPEI (Polyplus, France). Then, two different sets of primers (E1A-1 and E1A-2) specific to the E1A were used to measure an expression level of mRNA.

PCR was performed using HT1080 cells (HT) as the negative control, HEK293 cells (293) as the positive control, and plasmid gE1 in the form of genomic DNA as the control to avoid contamination of the plasmid. The results are shown in FIG. 5.

Figure 5:
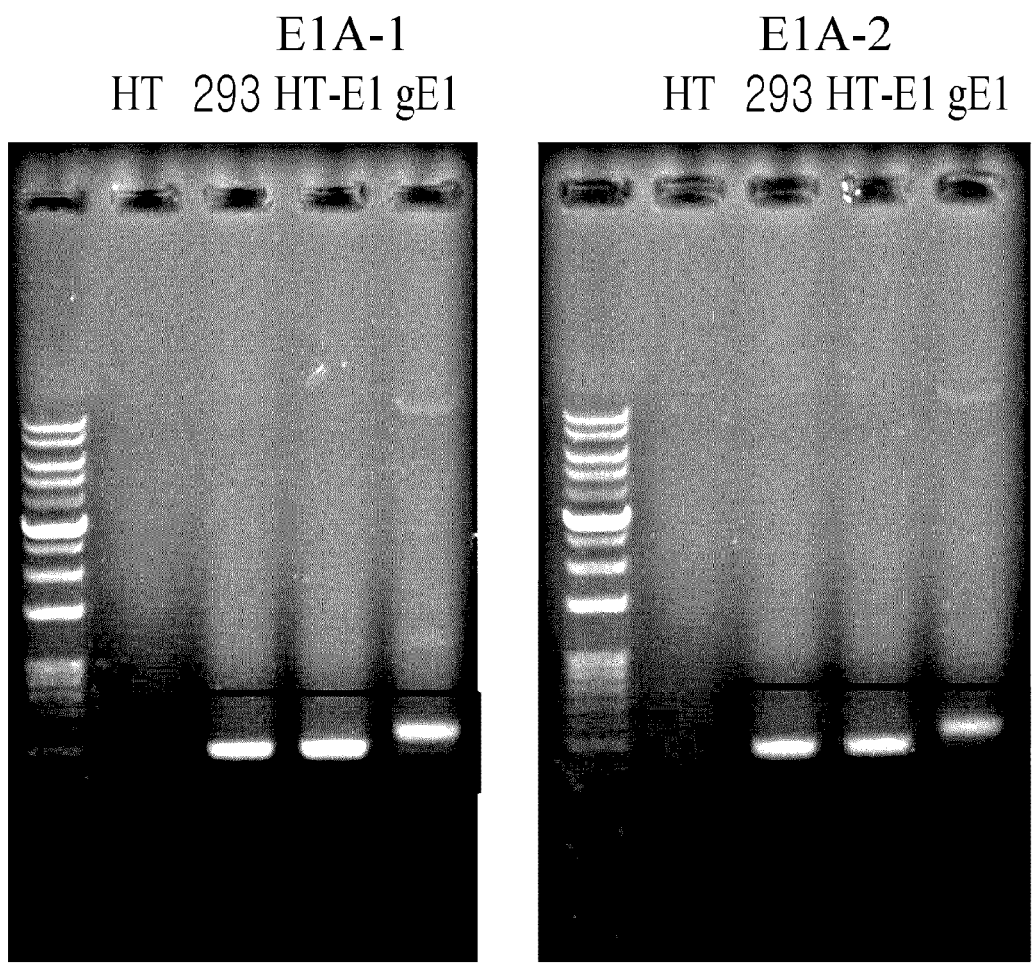
FIG. 5 shows the results of determining expression of the E1 gene in HT1080 cells (HT), HEK293 cells (293), HT1080 cells transfected with a retroviral vector including the E1 gene (HT-E1), and a plasmid in the form of genomic DNA (gE1).

Referring to FIG. 5, it can be seen that, when the HT1080 cells (as the negative control) were transfected with the retroviral vector (HT-E1), a band was observed in the same size as the HEK293 cells. From these result, it can be seen that the E1 gene was introduced and expressed by the cloned gene.

A retrovirus-producing packaging cell line was transfected with each of the retroviral vectors into which the E1A and E1B genes of Example 1-1 were cloned, and then cultured to obtain the genes. DNA was extracted from a colony of the cultured cells using a mini-prep method, digested with a restriction enzyme, and then subjected to electrophoresis. The corresponding size was able to be measured to determine whether the E1A and E1B genes were introduced (FIG. 6)

Referring to FIG. 6, it can be seen that the E1A or E1B gene was introduced into the retrovirus-producing cells via the retroviral vector.

Example 2: Selection of Adenovirus-Producing Cell Line

At least ten normal cell lines were purchased from the American Type Culture Collection (ATCC, USA), and proliferation capacities of the normal cell lines were evaluated by an MTT assay or the like to select six normal cell lines having an excellent proliferation capacity. The six selected cell lines were primarily transfected with each of the two E1 gene-expressing retroviruses prepared in Example 1, and then treated with G418 (Sigma, USA) to select cells into which the E1 gene was inserted.

mRNAs were isolated from the selected cells, and expression levels of E1A, E1B19K, and E1B55K were compared to those of the HEK293 cells. A method of transfecting each of the cell lines with each of the retroviruses expressing the E1, E1A, and E1B genes and selecting the cells based on the expression levels of the E1, E1A, and E1B genes was repeated.

In this case, the expression levels of E1A, E1B19K, and E1B55K were compared by means of real-time PCR and western blotting to select the cell lines having an expression level of 80% or more.

Example 3: Production of Adenovirus from Cell Line for Producing Adenovirus Having Reduced Autoreplication Capability L132 cells were infected with the retrovirus obtained by the method of Example 1, and then transfected with an adenoviral vector to prepare a cell line for producing an adenovirus having a reduced autoreplication capability. A titer of the produced adenovirus was measured to check whether the adenovirus was produced in the established cell line.

The results of experiments when the L132 cells were infected only with the E1 retrovirus; and when the L132 cells were infected with the E1 retrovirus followed by further infection with the E1A retrovirus using the method of the present invention were compared. The results are shown in FIGS. 7 to 9.

Referring to FIGS. 7 and 8, it can be seen that an amount of produced adenovirus in the $6^{th}$ cell line (#6) was 2.9 times larger when the cell line was further infected with the E1A retrovirus.

Also, it can be seen that an amount of produced adenovirus in the $11^{th}$ cell line (#11) was 3.8 times larger when the cell line was further infected with the E1A retrovirus.

FIG. 9 is a graph showing the amounts of the produced adenoviruses in the two cases. Also, it can be seen that the cell line further infected with the E1A retrovirus had a high level of adenoviral titer.

Therefore, from these results, it can be seen that the adenovirus-producing ability was able to be enhanced by additionally inserting the E1A gene using the retrovirus according to the present invention.

Example 4: RCA Inspection of Produced Adenovirus

For RCA inspection, a total of six clones (one for each cell line) were selected from the cell lines, and then passed at least five times to produce the adenoviruses depending on the passages.

When the adenovirus-producing cell line had a cytopathic effect (CPE) after the cell line was infected with the adenoviral vector as described in Examples 1 to 3, the cells were harvested and sonicated to obtain a supernatant. Thereafter, the supernatant was concentrated with CsCl and purified using an ultracentrifuge to obtain the produced adenovirus.

PCR was performed using specific primers to determine whether or not the produced virus had the E1 gene. In this case, HEK293 cells were used as the positive control. From the results of inspection, it was confirmed that the adenovirus produced in the cell line for producing an adenovirus according to the present invention did not have the E1 gene.

Example 5: Stable Cell Line for Producing Adenovirus Having Reduced Autoreplication Capability 5-1: Analysis of E1 and E1A Genes in GT541 Cell Line The E1 and E1A genes were cloned into the retroviral vector as described in Example 1-1. When the genes were delivered through the retroviral vector, the gene (E1) inserted into the retroviral vector was inserted into the genomic DNA of the host cell. Therefore, to determine whether the E1 and E1A genes were inserted into the GT541 clone (referred to as a cell line in which E1 was introduced into L132 cells), cellular gDNA was extracted (using a Qiagene Tissue kit), and then subjected to PCR using the following corresponding primers (see Tables 1 and 2)

TABLE 1

| E1 Primer sequences (2,962 bp) | |
|---|---|
| E1 (Forward) (0 to 33 bp) | GGA TCC ATG AGA CAT ATT ATC TGC CAC GGA GGT (33 mers) (SEQ ID NO: 3) |
| E1 (Reverse) (2,930 to 2,962 bp) | GAA TTC TCA ATC TGT ATC TTC ATC GCT AGA GCC (33 mers) (SEQ ID NO: 4) |

TABLE 2

| E1A Primer sequences (421 bp) | |
|---|---|
| E1A (Forward) (78 to 101 bp) | CGA AGA GGT ACT GGC TGA TAA TCT (24 mers) (SEQ ID NO: 5) |
| E1A (Reverse) (480 to 499 bp) | CCG TAT TCC TCC GGT GAT AA (20 mers) (SEQ ID NO: 6) |

PCR was performed using L132 cells (L132) as the negative control, HEK293A cells (293A) as the positive control, and a cell line (named '1132-2E1-3E1A#6') in which the E1 and E1A genes were inserted into L132 cells as the experimental group. The results are shown in FIG. 10.

FIG. 10 shows the results of subjecting the PCR product to electrophoresis to confirm the presence of the E1 and E1A genes. As shown in FIGS. 10A and 10B, it can be seen that bands corresponding to the E1 gene (2,962 bp) and the E1A gene (421 bp) were observed in the GT541 clone (L132-2E1-3E1A#6).

As a result, it can be seen that the E1 and E1A genes were introduced and expressed in the L132 cells.

5-2: RCA Test

To check whether an RCA reaction occurred in the cell line of Example 5-1, the cell line was infected with Ad-GFP, and the viruses were harvested. Thereafter, gDNA was extracted from the harvested viruses, and then subjected to a PCR method using the primers corresponding to the E1 gene.

From the corresponding experiment, it was confirmed using the primer sequences (241 bp) for verification of E1 RCA that the RCA reaction occurred (see Table 3)

TABLE 3

| | Primer sequences (241 bp) for verification of E1 RCA |
|---|---|
| E1 (RCA) (Forward) | ATG AGA CAT ATT ATC TGC CAC (21 mers) (SEQ ID NO: 7) |
| E1 (RCA) (Reverse) | GTA AGT CAA TCC CTT CCT GCA C (22 mers) (SEQ ID NO: 8) |

PCR was performed using viral gDNA (named '293A') extracted after 293A cells were infected with the virus, DNA of 293A cells extracted as the positive control (named '293A cells'), and a GT541 cell line (named '1132-2E1-3E1A#6') as the experimental group. The results are shown in FIG. 11.

Referring to FIG. 11, an RCA reaction, that is, a band of E1 (241 bp), was found only in the 293A cells, and was not found in the other cells. As a result, it can be seen that the RCA reaction did not occur in the GT541 cell line.

5-3: Measurement of Adenoviral Titer

To determine whether the adenovirus was produced in the cell line of Example 5-1, a titer of the produced adenovirus was measured.

The cell lines were cultured, and infected with Ad-GFP. Then, the cells were harvested, and then stored at −70° C. The next day, the cells were lysed using a sonicator, and centrifuged to obtain a supernatant. Then, gDNA was extracted from the supernatant, and then quantified using real-time PCR.

Figure 12:
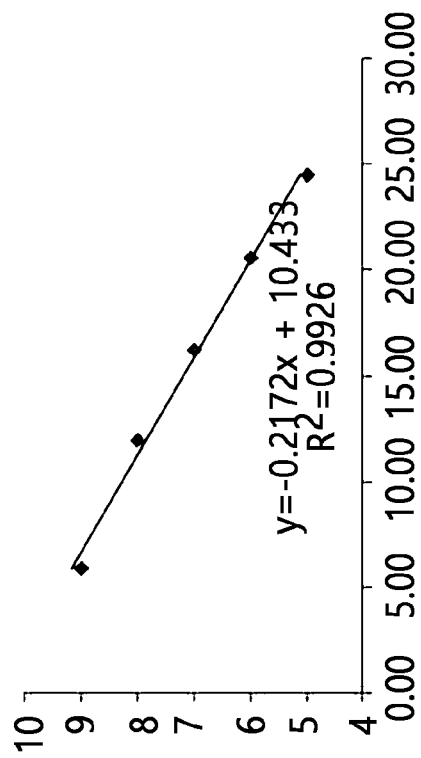
FIG. 12 shows the results of determining the titer of adenovirus produced in the cell line for producing an adenovirus, in which L132 cells were transfected with an E1 retrovirus, followed by additional transfection with an E1A retrovirus.

FIG. 12 shows the results of comparing L132-2E1-3E1A#6 and HEK 293A cells (named '293A') widely used as the adenoviral host cells.

Referring to FIG. 12, it can be seen that an amount of the adenovirus produced in the 293A was $8.53 \times 10^9$ GC/mL, and an amount of the adenovirus produced in the L132-2E1-3E1A#6 was $2.53 \times 10^9$ GC/mL.

Therefore, from the results, it can be seen that the adenovirus-producing cell line had a high adenovirus-producing ability when the cells were infected with the E1 retrovirus, followed by further infection with the E1A retrovirus, and also that the adenovirus-producing cell line was able to be used as the adenovirus cell line having high stability because the adenovirus-producing cell line had no RCA reaction.

The invention claimed is:

1. A cell line for producing an adenovirus, comprising:
   i) an E1 gene of 2962 bp including both an E1A gene and an E1B gene; and
   ii) an E1A gene of 998 bp that is separate from the E1A gene of i) above, an E1B gene of 1808 bp that is separate from the E1B gene of i) above, or both,
   wherein the cell line does not generate replication competent adenovirus (RCA).

2. The cell line of claim 1, wherein the E1 gene is adenovirus type 5.

3. The cell line of claim 1, wherein the E1A gene is the nucleic acid sequence of SEQ ID NO: 1.

4. The cell line of claim 1, wherein the E1B gene is the nucleic acid sequence of SEQ ID NO: 2.

5. The cell line of claim 1, wherein the cell line is a human-derived cell line.

6. The cell line of claim 5, wherein the cell line is an L132 cell line.

7. A packaging composition for producing a recombinant adenovirus, comprising:
   the cell line of any one of claims 1 to 6; and
   an adenoviral vector.

8. A method of preparing a cell line for producing an adenovirus, the method comprising:
   (a) preparing i) a first retrovirus vector comprising an E1A gene of 998 bp or an expression product thereof, ii) a second retrovirus vector comprising an E1B gene of 1808 bp or an expression product thereof, and iii) a third retrovirus vector comprising an E1 gene of 2962 bp including both the E1A gene and the E1B gene or an expression product thereof;
   (b) transfecting the first, second, and third retrovirus vectors into cell lines for producing retroviruses to thereby obtain a first retrovirus, a second retrovirus, and a third retrovirus, respectively;
   (c) infecting a cell line for producing an adenovirus with the third retrovirus; and
   (d) further infecting the cell line for producing an adenovirus with the first retrovirus, the second retrovirus, or both, to thereby obtain the cell line that (1) comprises:
   i) an E1 gene of 2962 bp including both an E1A gene and an E1B gene; and
   ii) an E1A gene of 998 bp that is separate from the E1A gene of i) above, an E1B gene of 1808 bp that is separate from the E1B gene of i) above, or both,
   wherein the cell line is capable of producing the adenovirus, and does not generate replication competent adenovirus (RCA).

9. The method of claim 8, wherein the E1A gene is the nucleic acid sequence of SEQ ID NO: 1 and wherein the E1B gene is the nucleic acid sequence of SEQ ID NO: 2.

10. The method of claim 8, wherein the cell line of (c) is a human-derived cell.

11. The method of claim 10, wherein the cell line is an L132 cell line.

12. A packaging composition for adeno-associated virus (AAV) production comprising:
   an adenovirus obtained from a cell line for producing an adenovirus wherein the cell line does not generate replication competent adenovirus (RCA) and the cell line comprises:
   i) an E1 gene of 2962 bp including both an E1A gene and an E1B gene; and
   ii) an E1A gene of 998 bp that is separate from the E1A gene of i) above, an E1B gene of 1808 bp that is separate from the E1B gene of i) above, or both;
   a cell line comprising a nucleic acid sequence of a rep gene of the AAV and a nucleic acid sequence of a cap gene of the AAV; and
   an AAV vector.

13. A composition for gene therapy comprising
   an adenovirus obtained from a cell line for producing an adenovirus,
   wherein the cell line does not generate replication competent adenovirus (RCA) and the cell line comprises:
   i) an E1 gene of 2962 bp including both an E1A gene and an E1B gene; and
   ii) an E1A gene of 998 bp that is separate from the E1A gene of i) above, an E1B gene of 1808 bp that is separate from the E1B gene of i) above, or both.

* * * * *

SEQUENCE LISTING

```
<160> NUMBER OF SEQ ID NOS: 8

<210> SEQ ID NO 1
<211> LENGTH: 998
<212> TYPE: DNA
<213> ORGANISM: Artificial Sequence
<220> FEATURE:
<223> OTHER INFORMATION: Adenovirus type 5

<400> SEQUENCE: 1
ggatccatga gacatattat ctgccacgga ggtgttatta ccgaagaaat ggccgccagt      60
cttttggacc agctgatcga agaggtactg gctgataatc ttccacctcc tagccatttt     120
gaaccaccta cccttcacga actgtatgat ttagacgtga cggccccga agatcccaac     180 gaggaggcgg tttcgcagat tttcccgac tctgtaatgt tggcggtgca ggaagggatt     240
gacttactca cttttccgcc ggcgcccggt tctccggagc cgcctcacct ttcccggcag     300
cccgagcagc cggagcagag agccttgggt ccggtttcta tgccaaacct tgtaccggag     360
gtgatcgatc ttacctgcca cgaggctggc tttccaccca gtgacgacga ggatgaagag     420
ggtgaggagt ttgtgttaga ttatgtggag caccccgggc acggttgcag gtcttgtcat     480
tatcaccgga ggaatacggg ggaccagat attatgtgtt cgctttgcta tatgaggacc     540
tgtggcatgt ttgtctacag taagtgaaaa ttatgggcag tgggtgatag agtggtgggt     600
ttggtgtggt aattttttt ttaattttta cagttttgtg gtttaaagaa ttttgtattg     660
tgattttttt aaaaggtcct gtgtctgaac ctgagcctga gcccgagcca gaaccggagc     720
ctgcaagacc tacccgccgt cctaaaatgg cgcctgctat cctgagacgc ccgacatcac     780
```

| | | |
|---|---|---|
| ctgtgtctag agaatgcaat agtagtacgg atagctgtga ctccggtcct tctaacacac | 840 |
| ctcctgagat acacccggtg gtcccgctgt gccccattaa accagttgcc gtgagagttg | 900 |
| gtgggcgtcg ccaggctgtg gaatgtatcg aggacttgct taacgagcct gggcaacctt | 960 |
| tggacttgag ctgtaaacgc cccaggccat aagaattc | 998 |

```
<210> SEQ ID NO 2
<211> LENGTH: 1808
<212> TYPE: DNA
<213> ORGANISM: Artificial Sequence
<220> FEATURE:
<223> OTHER INFORMATION: Adenovirus type 5

<400> SEQUENCE: 2
```

| | | |
|---|---|---|
| ggatccatgg aggcttggga gtgtttggaa gattttttctg ctgtgcgtaa cttgctggaa | 60 |
| cagagctcta acagtaccct ttggttttgg aggtttctgt ggggctcatc ccaggcaaag | 120 |
| ttagtctgca gaattaagga ggattacaag tgggaatttg aagagctttt gaaatcctgt | 180 |
| ggtgagctgt ttgattcttt gaatctgggt caccaggcgc ttttccaaga aaggtcatc | 240 |
| aagactttgg attttccac accggggcgc gctgcggctg ctgttgcttt tttgagtttt | 300 |
| ataaaggata aatggagcga agaaacccat ctgagcgggg ggtacctgct ggattttctg | 360 |
| gccatgcatc tgtggagagc ggttgtgaga cacaagaatc gcctgctact gttgtcttcc | 420 |
| gtccgcccgg cgataatacc gacggaggag cagcagcagc agcaggagga agccaggcgg | 480 |
| cggcggcagg agcagagccc atggaacccg agagccggcc tggaccctcg ggaatgaatg | 540 |
| ttgtacaggt ggctgaactg tatccagaac tgagacgcat tttgacaatt acagaggatg | 600 |
| ggcaggggct aaaggggta aagagggagc ggggggcttg tgaggctaca gaggaggcta | 660 |
| ggaatctagc ttttagctta atgaccagac accgtcctga gtgtattact tttcaacaga | 720 |
| tcaaggataa ttgcgctaat gagcttgatc tgctggcgca gaagtattcc atagagcagc | 780 |
| tgaccactta ctggctgcag ccaggggatg atttttgagga ggctattagg gtatatgcaa | 840 |
| aggtggcact taggccagat tgcaagtaca agatcagcaa acttgtaaat atcaggaatt | 900 |
| gttgctacat ttctgggaac ggggccgagg tggagataga tacggaggat agggtggcct | 960 |
| ttagatgtag catgataaat atgtggccgg gggtgcttgg catggacggg gtggttatta | 1020 |
| tgaatgtaag gtttactggc cccaatttta gcggtacggt tttcctggcc aataccaacc | 1080 |
| ttatcctaca cggtgtaagc ttctatgggt ttaacaatac ctgtgtggaa gcctggaccg | 1140 |
| atgtaagggt tcggggctgt gccttttact gctgctggaa ggggtggtg tgtcgcccca | 1200 |
| aaagcagggc ttcaattaag aaatgcctct ttgaaaggtg taccttgggt atcctgtctg | 1260 |
| agggtaactc caggggtgcgc cacaatgtgg cctccgactg tggttgcttc atgctagtga | 1320 |
| aaagcgtggc tgtgattaag cataacatgg tatgtggcaa ctgcgaggac agggcctctc | 1380 |
| agatgctgac ctgctcggac ggcaactgtc acctgctgaa gaccattcac gtagccagcc | 1440 |
| actctcgcaa ggcctggcca gtgtttgagc ataacatact gacccgctgt tccttgcatt | 1500 |
| tgggtaacag gagggggtg ttcctaccctt accaatgcaa tttgagtcac actaagatat | 1560 |
| tgcttgagcc cgagagcatg tccaaggtga acctgaacgg ggtgtttgac atgaccatga | 1620 |
| agatctggaa ggtgctgagg tacgatgaga cccgcaccag gtgcagaccc tgcgagtgtg | 1680 |
| gcggtaaaca tattaggaac cagcctgtga tgctggatgt gaccgaggag ctgaggcccg | 1740 |
| atcacttggt gctggcctgc acccgcgctg agtttggctc tagcgatgaa gatacagatt | 1800 | gagaattc                                                              1808

<210> SEQ ID NO 3
<211> LENGTH: 33
<212> TYPE: DNA
<213> ORGANISM: Artificial Sequence
<220> FEATURE:
<223> OTHER INFORMATION: E1 forward primer

<400> SEQUENCE: 3
ggatccatga gacatattat ctgccacgga ggt                                  33

<210> SEQ ID NO 4
<211> LENGTH: 33
<212> TYPE: DNA
<213> ORGANISM: Artificial Sequence
<220> FEATURE:
<223> OTHER INFORMATION: E1 reverse primer

<400> SEQUENCE: 4
gaattctcaa tctgtatctt catcgctaga gcc                                  33

<210> SEQ ID NO 5
<211> LENGTH: 24
<212> TYPE: DNA
<213> ORGANISM: Artificial Sequence
<220> FEATURE:
<223> OTHER INFORMATION: E1A forward primer

<400> SEQUENCE: 5
cgaagaggta ctggctgata atct                                            24

<210> SEQ ID NO 6
<211> LENGTH: 20
<212> TYPE: DNA
<213> ORGANISM: Artificial Sequence
<220> FEATURE:
<223> OTHER INFORMATION: E1A reverse primer

<400> SEQUENCE: 6
ccgtattcct ccggtgataa                                                 20

<210> SEQ ID NO 7
<211> LENGTH: 21
<212> TYPE: DNA
<213> ORGANISM: Artificial Sequence
<220> FEATURE:
<223> OTHER INFORMATION: E1(RCA) forward primer

<400> SEQUENCE: 7
atgagacata ttatctgcca c                                               21

<210> SEQ ID NO 8
<211> LENGTH: 22
<212> TYPE: DNA
<213> ORGANISM: Artificial Sequence
<220> FEATURE:
<223> OTHER INFORMATION: E1(RCA) reverse primer

<400> SEQUENCE: 8
gtaagtcaat cccttcctgc ac                                              22